United States Patent
Moon et al.

(10) Patent No.: US 6,582,961 B1
(45) Date of Patent: Jun. 24, 2003

(54) METHODS OF PROTECTING PLANTS FROM PATHOGENS

(75) Inventors: Darin J. Moon, Burley, ID (US); Anne J. Anderson, Providence, UT (US)

(73) Assignee: Redox Chemicals, Inc., Burley, ID (US)

( * ) Notice: Subject to any disclaimer, the term of this patent is extended or adjusted under 35 U.S.C. 154(b) by 0 days.

(21) Appl. No.: 09/857,137

(22) PCT Filed: Dec. 2, 1999

(86) PCT No.: PCT/US99/28552

§ 371 (c)(1),
(2), (4) Date: Sep. 17, 2001

(87) PCT Pub. No.: WO00/32048

PCT Pub. Date: Jun. 8, 2000

Related U.S. Application Data (60) Provisional application No. 60/110,835, filed on Dec. 3, 1998.

(51) Int. Cl.[7] .................. C12N 5/00; A01N 25/00; A01N 63/00; A61K 31/60; A61K 31/19
(52) U.S. Cl. ............ 435/431; 435/70.1; 435/420; 424/405; 424/93.4; 424/93.46; 514/159; 514/165; 514/557
(58) Field of Search .............. 435/70.1, 420, 435/431; 424/405, 93.4, 93.46; 514/159, 165, 557

(56) References Cited

U.S. PATENT DOCUMENTS

| | | | | |
|---|---|---|---|---|
| 5,607,856 A | * | 3/1997 | Moon et al. | |
| 5,693,318 A | * | 12/1997 | Burke et al. | |
| 5,959,187 A | * | 9/1999 | Bailey et al. | |
| 6,136,552 A | * | 10/2000 | Klessig et al. | |
| 6,277,814 B1 | * | 8/2001 | Qui et al. | |

OTHER PUBLICATIONS

Klessig et al. Plant Mol. Biol. 1994. vol. 26, pp. 1439–1458.*
Raskin, I. Annual Rev. Plant Physiol. Plant Mol. Biol. 1992. vol. 43, pp. 439–463.*

* cited by examiner

Primary Examiner—Christopher R. Tate
(74) Attorney, Agent, or Firm—Townsend and Townsend and Crew LLP (57) ABSTRACT

This invention provides novel methods for improving plant quality and yield in the presence of pathogens. The method increases the levels of pathogenesis-related proteins, such as PR1, phenylalanine ammonia lyase, or plant cell wall proteins such as hydroxyproline-rich glycoproteins, in a plant by contacting the plant with a plant systemic inducer and a reactive oxygen species wherein the amount of the reactive oxygen species is sufficient to increase the amount of the pathogenesis-related protein above the level induced by the plant systemic inducer in the absence of the reactive oxygen species. A preferred reactive oxygen species is peracetic acid; a preferred plant systemic inducer is salicylic acid.

46 Claims, 4 Drawing Sheets

PR1-a

| 3,500 PAA | 10,000 PAA | 3,500 +SA | 10,000 +SA | No PAA +SA |
|---|---|---|---|---|

FIG. 1.

PAL

| H$_2$O | 3,500 PAA | 10,000 PAA | 3,500 ppm +SA |
|---|---|---|---|

FIG. 2

Hydroxyproline rich glycoprotein

| H$_2$O | 3,500 PAA | 10,000 PAA | 3,500 +SA | 10,000 +SA | No PAA +SA |

METHODS OF PROTECTING PLANTS FROM PATHOGENS

CROSS-REFERENCES TO RELATED APPLICATIONS

This case is a continuation in part of provisional patent application serial No. 60/110,835, filed Dec. 3, 1998, the contents of which are incorporated by reference.

STATEMENT AS TO RIGHTS TO INVENTIONS MADE UNDER FEDERALLY SPONSORED RESEARCH AND DEVELOPMENT

Not applicable.

BACKGROUND OF THE INVENTION

1. Field of the Invention

This invention relates to methods for increasing resistance of plants to plant pathogens. More specifically, this invention relates to the surprising discovery that the application to plants of one or more reactive oxygen species and of one or more plant systemic inducers, either simultaneously or within a short time of each other, results in an increase in the level of pathogenesis-related proteins and of systemic acquired resistance in the plants over the effect of either one alone.

2. Background

Commercial cultivation of plants is a major part of the economy, encompassing not only crops grown for human food and animal feed, but also those, like cotton, grown for fiber, and others, such as flowers, grown for beauty. The importance of plants to people and to the economy can hardly be overstated. Plants are, however, also subject to constant attack by insects, fungi, bacteria, viruses, nematodes, and other pathogens. When pathogens find susceptible plants, these attacks can result in the loss of yield and quality, and may result in the loss of entire crops. These losses result in substantial economic harm to the growers and, in some areas of the world, contribute to famine.

Except for those farmers who practice organic farming, most attempts to control pathogens involve the use of pesticides, such as fungicides and insecticides. Many pesticides, however, have been withdrawn from the market because they have undesirable environmental impacts, and many currently on the market are being scrutinized for their environmental impact and may be withdrawn in the future. In addition, few, if any, pesticides are effective against the full range of pests which may attack a given crop from sowing to harvest to post-harvest storage. Thus, a number of different pesticides with different target organisms may need to be applied. Each one must be applied at the correct time in the growth of the plants to provide effective control of the target organism, each has its own requirements for handling and application, and each may require different, specialized equipment. Moreover, many pesticides are toxic or have toxic residues, and their use is therefore often restricted to certain windows of time before harvest, after which they cannot be used because of the potential danger to the consumer. During this window, the crop may be essentially unprotected, or yet another agent, safer for use close to harvesting, may be needed. The use of traditional chemical agents therefore requires complicated planning, careful timing, and considerable effort.

While pesticides form the bulk of attempts by farmers to protect plants from pathogenic attack, not all protection of plants against pathogens comes from the application of pesticides. For decades, it has been known that plants also have a wide variety of structural and biochemical defenses against attack by pathogens. See, e.g., Agrios, G., *Plant Pathology*, Academic Press, San Diego Calif. (3rd ed., 1988).

One of the biochemical defenses produced by plants in response to attack is induced resistance, in which plants which have been inoculated with biological agents or pretreated with various chemicals develop nonspecific resistance not only to the initial agent itself, but also to a variety of pathogenic agents, such as viruses, fungi, bacteria, and some insects. Induced resistance usually commences in the area around the initial inoculation, but over the course of a few days, may spread to portions of the plant not inoculated, a phenomenon known as systemic induced resistance, or as systemic acquired resistance ("SAR").

A number of compounds, such as salicylic acid, can induce resistance. See, e.g., Klessig, D. and Malamy, J., Plant Mol. Biol., 26:1439–1458 (1994); Raskin, I., Annu. Rev. Plant Physiol. Plant Mol. Biol. 43:439–463 (1992). They can be used to induce local resistance, by injection or spraying, or to induce SAR when absorbed, for example, through the roots. See generally, Agrios, supra, at Chapters 5 and 9. SAR develops some 7 days or more after exposure to the inoculant or chemical agent, and usually lasts for some 3 to 5 weeks. Id.

Because SAR protects plants against many different pests, increasing SAR in crops could potentially decrease or even eliminate the need to apply toxic pesticides. Further, since SAR protects against a multitude of pathogens, inducing SAR can eliminate the need for a number of separate agents which would otherwise be necessary to protect a crop, or reduce the amount of the separate agents which would otherwise be required. And, because the induction of SAR can essentially be performed by repetitive action, use of this technique would demand far less effort for the farmer than the currently required regimen of applying multiple agents, each with their own directions for handling, timing, amounts, concentrations, methods of application, and possible adverse interactions.

One of the world's largest pharmaceutical companies has made an effort to develop the use of systemic inducers to protect crops in the field. To this end, it is bringing to market a systemic inducer, benzothiadiazole, under the trade name Actigard.™ But, the manufacturer now recommends that Actigard™ be used in combination with conventional chemical agents in providing protection to crops. Thus, even a systemic inducer specifically selected, developed and tested for protection of crops has not eliminated the need for conventional pesticides even during the time the systemic inducer is being applied.

U.S. Pat. No. 5,607,856, teaches compositions and methods for sterilizing soil using oxygen radicals. The method involves contacting the soil with a solution of an activated oxygen species, a water-soluble phenolic complex extracted from a material such as humic material, a divalent cation, and a cation redox reducing agent.

What is needed in the art is a means of protecting a variety of crops, flowers, decorative and other plants in the field from pathogens more effectively, at lower cost, and with less effort than by the use of pesticides and other traditional chemical agents. Moreover, what is needed is a means of providing this protection with lower and less lasting damage to the environment than caused by such conventional agents. What is further needed is a means of increasing the protection of crops from pathogens to levels above the levels obtainable by the use of systemic inducers alone, to more crops than can be protected by the use of systemic inducers alone, and against a wider range of pathogens. The present invention addresses these and other needs.

SUMMARY OF THE INVENTION

This invention provides novel methods of protecting plants from pathogens. In one group of embodiments, the methods involve contacting the foliage of a plant with a plant systemic inducer and a reactive oxygen species, where the amount of the reactive oxygen species is sufficient to increase the expression of phenylalanine ammonia lyase, glutathione S-transferase, hydroxyproline-rich glycoprotein, chalcone synthase, or pathogenesis-related proteins, in the plant above the level which would be induced by the plant systemic inducer in the absence of the reactive oxygen species. The invention further provides a method of contacting a plant with a plant systemic inducer and a reactive oxygen species, where the amount of the systemic plant inducer is sufficient to increase the expression of phenylalanine ammonia lyase, glutathione S-transferase, hydroxyproline-rich glycoprotein, chalcone synthase, or pathogenesis-related proteins in the plant above the level which would be induced by the reactive oxygen species in the absence of the plant systemic inducer. The increase in pathogenesis-related proteins, phenylalanine ammonia lyase, glutathione S-transferase, or hydroxyproline-rich glycoprotein caused by contacting a plant with both a plant systemic inducer and a reactive oxygen species may be additive compared to the level induced by either the systemic inducer in the absence of the reactive oxygen species or by the reactive oxygen species in the absence of the systemic inducer, or they may be greater than an amount which would be additive.

The plant can be edible by humans or by animals, can be grown for fiber content, such as cotton, can be used for or processed to become a medicine or medicament, or can be for decorative, ornamental, or recreational use, such as turf grass, house plants, flowers, or Christmas trees.

The reactive oxygen species ("ROS") can be peracetic acid, hydrogen peroxide, a hydroperoxide, a peroxide, or a phenolic hydroperoxide; ozone is not preferred as an ROS. The plant systemic inducer can be salicylic acid, jasmonic acid, isonicotinic acid, dichloroisonicotinic acid, benzothiadiazole, phosphorous acid, arachidonic acid, or cinnamic acid, can be derived from kelp or other seaweed, or can be a beneficial microbe. The systemic inducer can be humic acid, or can be used in combination with humic acid. The ROS and microbial plant systemic inducer can be administered about 24 hours of one another, whereas an ROS and a chemical plant systemic inducer are preferably administered within one hour of each other and even more preferably are administered together in a mixture, either as, for example, a powder, or, more preferably, a solution. The pathogenesis-related protein can be a product of any of the PR genes having or thought to have a role in protecting plants from pathogens, such as the PR-1, PR-2, PR-3, PR-4 and PR-5 genes. The proteins induced can also be phenylalanine ammonia lyase, chalcone synthase, or a hydroxyproline-rich glycoprotein or other proteins related to strengthening of cell walls or plant defense.

The invention further provides a composition for foliar application to plants comprising a plant systemic inducer and a reactive oxygen species wherein the amount of reactive oxygen species is sufficient to increase the level of a natural plant product selected from the group consisting of: phenylalanine ammonia lyase; hydroxyproline-rich glycoproteins, glutathione S-transferase, chalcone synthase, and pathogenesis-related proteins to a level above the level induced by the plant systemic inducer in the absence of the reactive oxygen species. The composition can further comprise an aqueous solution and detergents, chelating agents or sequestering agents.

In another group of embodiments, the invention provides methods of protecting a plant by contacting one or more roots of a plant with a plant systemic inducer and a reactive oxygen species, where the amount of the reactive oxygen species (ROS) is sufficient to increase the expression of phenylalanine ammonia lyase, glutathione S-transferase, hydroxyproline-rich glycoprotein, chalcone synthase, or pathogenesis-related proteins, in the plant above the level which would be induced by the plant systemic inducer in the absence of the reactive oxygen species, provided that the composition does not comprise an exogenous agent selected from the group comprising a cation redox reducing agent and a divalent cation having redox potential in amounts sufficient to reduce the levels of microorganisms in soil around the roots by 40% or more. The invention further provides a method of contacting one or more roots of a plant with a plant systemic inducer and a reactive oxygen species, where the amount of the systemic plant inducer is sufficient to increase the expression of phenylalanine ammonia lyase, glutathione S-transferase, hydroxyproline-rich glycoprotein, chalcone synthase, or pathogenesis-related proteins in the plant above the level which would be induced by the reactive oxygen species in the absence of the plant systemic inducer, provided that the composition does not comprise an agent selected from the group comprising a cation redox reducing agent and a divalent cation having redox potential in amounts sufficient to reduce the levels of microorganisms in soil around the roots by 40% or more. The systemic inducer can be, or can be mixed with, humic acid.

The invention further provides compositions for soil application to plants comprising a plant systemic inducer and a reactive oxygen species wherein the amount of reactive oxygen species is sufficient to increase the level of a natural plant product selected from the group consisting of: phenylalanine ammonia lyase; hydroxyproline-rich glycoproteins, glutathione S-transferase, and pathogenesis-related proteins to a level above the level induced by the plant systemic inducer in the absence of the reactive oxygen species, provided that the compositions do not comprise an agent selected from the group comprising a cation redox reducing agent and a divalent cation having redox potential in amounts sufficient to reduce the levels of microorganisms in soil around the roots by 40% or more. The systemic inducer can be, or can be mixed with, humic acid.

BRIEF DESCRIPTION OF THE DRAWINGS

FIG. 1 is a northern blot of RNA probed for expression of PR-1a protein. RNA was extracted from 14 day-old red kidney bean plants 24 hours after leaves of the plants were sprayed until wet with one of five treatments. Lane 1: treatment with 3,500 ppm of peracetic acid ("PAA"). Lane 2: treatment with 10,000 ppm of PAA. Lane 3: treatment with 3,500 ppm of PAA plus 200 ppm of salicylic acid/humic acid mixture (see Example 1; hereafter "inducer mixture"). Lane 4: treatment with 10,000 ppm of PAA and 200 ppm of inducer mixture. Lane 5: treatment with 200 ppm inducer mixture, without PAA.

FIG. 2 is a northern blot of RNA probed for expression of phenylalanine ammonia lyase ("PAL"). RNA was extracted from 14 day-old red kidney bean plants 24 hours after leaves of the plants were sprayed until wet with one of four treatments. Lane 1: water-only control. Lane 2: treatment with 3,500 ppm of PAA. Lane 3: treatment with 10,000 ppm of PAA. Lane 4: treatment with 3,500 ppm of PAA plus 200 ppm of inducer mixture.

FIG. 3 is a northern blot of RNA probed for expression of hydroxyproline-rich glycoproteins ("HPRG" or "HYP"). RNA was extracted from 14 day-old red kidney bean plants 24 hours after leaves of the plants were sprayed until wet with one of five treatments. Lane 1: water-only control. Lane 2: treatment with 3,500 ppm of PAA. Lane 3: treatment with 10,000 ppm of PAA. Lane 4: treatment with 3,500 ppm of PAA plus 200 ppm of inducer mixture. Lane 5: treatment with 10,000 ppm of PAA plus 200 ppm of inducer mixture. Lane 6: treatment with 200 ppm of inducer mixture, without presence of PAA.

DETAILED DESCRIPTION

I. Introduction

This invention arises from the surprising discovery that the application to plants of one or more reactive oxygen species ("ROS") and of one or more systemic inducers, such as salicylic acid, either simultaneously or within a short time of each other, results in an increase in the level of transcription of hydroxyproline-rich glycoproteins ("HRGP"), phenylalanine ammonia lyase ("PAL"), chalcone synthase, peroxidase (PAL, chalcone synthase, and peroxidase are sometimes referred to as a plant's "phenolic defenses"), glutathione S-transferase, or pathogenesis-related proteins ("PR proteins"), and of SAR in the plants over the effect of either one alone. The increase is additive of the effects of ROS or of a systemic inducer alone and, even more surprisingly, may be synergistic.

This result could not have been predicted. What was known was that ROS and systemic inducers each cause a set of genes to be expressed, but some of the genes were the same and some were different for each class of agent. Since the mechanisms of signaling within the plant cell related to SAR are not yet elucidated, there was no way to predict whether applying both agents at or around the same time would result simply in the same amount of induction of SAR as applying one of the agents, or whether the amount induced would be greater than or less than applying one of these agents alone.

We have discovered, for example, that contacting plants with both agents results in increases in levels of transcription of PR proteins over that expected. "The expression of many of the well characterized PR genes (e.g. PR-1 through PR-5) in tobacco has been correlated with resistance to a large variety of viral, bacterial and fungal pathogens. As a result, expression of PR genes is often used as a marker for induction of disease resistance." Klessig and Malamy, supra, at 1441. See also, e.g., Bowles, D., Annu Rev. Biochem 59:873–907 (1990); Carr, J. and Klessig, D., The pathogenesis-related proteins of plants. In Setlow, J. (ed.) *Genetic Engineering Principles and Methods*, vol. 11, pages 65–109. Plenum Press, New York (1989); Dixon, R., et al., Adv Genet. 28:165–234 (1990); Ward, E., et al., Plant Cell 3:1085–1094 (1991); Ye, X., et al., Plant Sci., 84:1–9 (1992); Woloshuk, C., et al., Plant Cell 3:619–628 (1991); Alexander, D., et al, Proc Natl Acad Sci USA 90:7327–7331 (1993); Bol, J., et al., Annu Rev Phytopath 28:113–138 (1990); Ward, et al., Plant Cell 3:1085–1094 (1991); Niederman, et al., Plant Physiol 108:17–21 (1995); Lawton, et al., Plant J. 10:71–82 (1996); and Friedrich, L., et al., Plant J. 10:61–70 (1996).

We have shown that, in addition to the PR proteins, such as PR-1a, the transcription of other enzymes and proteins, such as PAL, chalcone synthase, and HRGP, increase in response to contacting plants with ROS and increase even more in response to contacting plants with both systemic plant inducers and ROS. The increases are greater than that induced by either class of agent alone, and may, indeed, be synergistic. And, while SAR is considered to take a week or more to develop, we have demonstrated that genes encoding the enzymes noted above are induced within 24 hours of contacting plants with these compositions. It is recognized in the art that the transcription of these genes is a marker for SAR.

In addition to these discoveries, a water soluble phenolic complex known as humic acid commercially sold as a fertilizer also acts as a systemic inducer. Contacting plants with humic acid induces changes in many of the same enzymes as those increased in response to previously known systemic plant inducers and that the levels of these enzymes increase even more when plants are contacted with both humic acid and ROS. As with previously known systemic inducers, the increases are greater than that induced by either class of agent alone, and may, indeed, be synergistic. Moreover, adding humic acid to a mixture of a previously known systemic inducer, such as salicylic acid, and an ROS results in yet a further improvement in the level of enzymes considered to be part of a plant's defense mechanisms.

The increases we have shown in the levels of PAL, HRGP, chalcone synthase, PR proteins or other marker proteins and enzymes upon application of the two types of agents is also mirrored in the field by levels of protection against pathogens comparable to or greater than the protection provided by conventional chemical agents directed against specific types of pathogens. As shown in the Examples, for instance, the application of a mixture of ROS and of a mixture of the systemic inducer salicylic acid and humic acid (hereafter "ROS/inducer mixture") to crops such as grapes, lettuce, tomatoes, carrots, and citrus fruit in field trials resulted in rates of infestation and amounts of damage from fungi, insects, and nematodes comparable to or lower than the rates of infestation and amounts of damage from the same pests to crops protected by conventional agents directed against those specific types of pathogens.

Moreover, this increased, and possibly synergistic effect allows the ROS and systemic inducers to be applied at rates which render them commercially viable compared to the pesticides, fungicides, or other agents which would otherwise be needed. Further, since ROS and systemic inducers are far less toxic to handle and apply than most conventional pesticides, use of the invention reduces the exposure of farmers and other agricultural workers to toxic chemicals they may be poorly trained or equipped to use. And, since SAR can be raised to protective levels by treatments (such as by the preferred embodiment of a mixture of an ROS and one or more SAR inducers) which are both relatively non-toxic to produce and much less environmentally damaging in use than many conventional pesticides and other chemical agents, the invention provides crops with meaningful protection from pathogens while sharply reducing the cost to the environment of that protection. Finally, as noted above, the protection has been demonstrated with respect to a variety of divergent plants and against a range of pathogens. The invention is therefore a significant and substantial improvement over the application of a systemic inducer alone.

It should be noted that increases in SAR in some cases may increase a plant's susceptibility to certain pathogens. But we predicted that this effect would be far outweighed by the increase in protection against a much wider range of pathogens than those to which a plant might become more susceptible, and that this effect would result in improved crop yield and quality. This prediction has been confirmed by the increases in crop yield and quality demonstrated in the field trials reported herein. Accordingly, the application of a systemic inducer and an ROS has been shown to have a positive effect in protecting crops in the field.

II. Definitions

The term "combining" as used herein refers to the mingling of two or more liquid, solid or aerosolized components before, during or after contact to plants.

The phrase "increase the level above the level induced by the plant systemic inducer in the absence of the reactive oxygen species" specifies a level of natural plant product. The level from which change is measured is the level of the natural plant product of interest that is induced in a plant by contact with a plant systemic inducer when a reactive oxygen species is absent. Therefore, the phrase quoted above refers to any concentration of a natural plant product that is above this level. Similarly, the phrase "increase the level above the level induced by the reactive oxygen species in the absence of the plant systemic inducer" specifies a level of natural plant product. The level from which change is measured is the level of the natural plant product of interest that is induced in a plant by contact with a reactive oxygen species when a plant systemic inducer is absent. Therefore, the phrase quoted above refers to any concentration of a natural plant product that is above this level.

The terms "administering" and "contacting" plants with a chemical or compound, as used herein, generally comprehend causing the plant to come into proximity with an exogenous liquid or solid (such as a powder) form of the chemical or compound. They do not comprehend the injection of compounds or chemicals into individual leaves or into individual plants.

The terms "hydroxyproline-rich glycoproteins" or "HRGPs," as used herein, refer to glycosylated proteins found in plant cell walls and associated with cell wall strengthening. The HRPGs are characterized by the presence of the motif: Ser-(Hyp)$_4$-Tyr, wherein "Hyp" is hydroxyproline.

The terms "pathogenesis-related protein," or "PR proteins," as used herein, refer to any of a number of families of proteins whose synthesis is considered in the art to be induced in response to, contact with, or infection by, a pathogen. They are considered to be encoded by, for example, the PR-1 to PR-5 genes. The expression of pathogenesis-related proteins may also be induced or increased in a plant by contacting the plant with plant systemic inducers, such as salicylic acid. The functions of many PR proteins are known. For example, the PR-2 genes encode hydrolytic β-1,3 glucanases, while the PR-3 family encodes chitanases. Other pathogenesis-related proteins, however, such as those expressed by the PR-1 gene group, have functions which have yet to be defined. Expression of PR-1a is, however, considered by those of skill in the art to be associated with, and a marker for, systemic acquired resistance.

The term "natural plant product," as used herein, refers to an enzyme or structural protein endogenously produced by a plant. Examples of such components include phenylalanine ammonia lyase, hydroxyproline-rich glycoproteins, and pathogenesis-related proteins.

As used herein, the term "pathogen resistance" refers to the ability of a plant to lessen the development of disease symptoms after exposure to a plant, insect or microbe.

The term "phenylalanine ammonia lyase" refers to an enzyme that catalyzes the conversion of phenylalanine into cinnamic acid. The enzyme, EC number 4.3.1.5., is involved in the formation of many classes of phenolic compounds involved in plant defense.

The term "glutathione S-transferase" refers to any of a family of enzymes which transfer glutathione in the course of any of various functions, including many involved in stress responses in plant cells. The enzymes play a role in oxidative stress, herbicide resistance and heavy metal tolerance. See, e.g., Neufield T, et al., J. Biol Chem 378:199–205 (1997); Chen W, et al., Plant Journal 10:955–966 (1996); Levine, A., et al., Cell 79:583–593 (1994).

The term "chalcone synthase" refers to an enzyme which is involved in the synthesis of more complex phenolic structures of chalcones essential for flavonoid synthesis. Flavonoids represent a major class of plant secondary metabolites that are important in plant survival. They are known to play a role in a wide range of plant functions, including pathogen protection. The enzyme, EC number 2.3.1.74, catalyzes the condensation of three molecules of malonyl-CoA with one molecule of 4-coumaroyl-CoA to produce chalcone. See, e.g., Hahlbrock K, Flavonoids. In Stumpf PK, Conn EE, eds, *Biochemistry of Plants*, Academic Press, New York (1981), pp 425–456; Niesbach-Klosgen U. et al., J Mol Evol 26:213–225 (1987).

The terms "plant systemic inducer," "systemic inducer of resistance," and "systemic inducer" are used herein as synonyms and as used herein refer to chemical or biological agents that induce pathogen resistance after a plant is contacted with a plant systemic inducer. Examples of chemical plant systemic inducers include, inter alia, salicylic acid, jasmonic acid, isonicotinic acid, dichloroisonicotinic acid, phosphorous acid, and cinnamic acid, chitosan, humic acid, and beta-1,3 glucans and other mixed glucans.

One skilled in the art will recognize that biological plant systemic inducers include, inter alia, bacteria, viruses, fungi, and nematodes. Kelp, a form of seaweed, and some other seaweeds, are rich sources of beta glucans and can be used as systemic inducers in the compositions and methods of the invention. Unlike bacteria, viruses, and most other microbiological agents, kelp and other seaweeds are sold commercially as fertilizers and are available as liquid extracts or as dried powders. In this regard, they more resemble agricultural chemicals and for ease of discussion, will therefore be treated as chemical inducers herein unless otherwise indicated. Finally, as noted in the Introduction, humic acid, a component found in the humus portion of some soils, also acts as a systemic inducer. Thus, the term "systemic inducer" can, where appropriate, include reference to humic acid. In preferred embodiments, we have found good results by including humic acid along with other systemic inducers in the compositions and methods of the invention. Accordingly, the addition of humic acid to other systemic inducers will generally be specifically denoted herein.

The phrase "reactive oxygen species" (abbreviated herein as "ROS") describes oxygenated compounds which serve as a source of oxygenated radicals. The term is considered to be synonymous with "activated oxygen species.," These compounds include, inter alia, peracetic acid, sodium peroxide, potassium oxide, potassium peroxide, calcium peroxide, magnesium peroxide, urea peroxide, hydrogen peroxide ($H_2O_2$), hydroperoxides (ROOH), peroxides (ROOR), and superoxides, where R is an alkane, alkene or alkyne, branched or unbranched, and of between 1 and 12 carbons and Ar is an aromatic ring, usually of 6 carbons, or a combination of such rings. As used herein, the term "reactive oxygen species" excludes the gas ozone.

Humus is the major organic component of soil. "Humic acid" is a phenolic complex which is a component of humus. Commercially, humic acid is generally extracted from what is described as a salt-free deposit of highly oxidized carbon known as "Leonardite." Extraction of humic acid from Leonardite is described in detail in U.S. Pat. No. 5,607,856.

"Peracetic acid" is a reactive oxygen species which is made by reacting glacial acetic acid with hydrogen peroxide. Since this reaction does not go to completion but instead results in a equilibrium being reached, at any point in time all three chemical species, peracetic acid, acetic acid, and hydrogen peroxide, will exist. Use of the term "peracetic acid" herein therefore encompasses mixtures of these three chemical species.

The phrase "field capacity" refers to the percent water remaining in the soil two to three days after having been saturated and after free drainage has practically ceased.

The term "foliar application" refers to the application of substances to the foliage, or above-ground portions, of plants, and especially application to the leaves of the plants. It is understood in the art that incidental amounts of substances used in foliar applications may filter to or contact the soil, but not in quantities which will permit penetration of the soil and significant contacting of the plant's roots compared to the amount contacting the leaves and other above-ground structures.

The term "soil application" refers to the application of a substance to the soil around a plant, where the intent is either to affect the soil directly or to place the roots of the plant in contact with the substance. Generally, substances applied through a soil application will not contact the foliage, but it is possible that incidental amounts of substances used in soil applications may contact the foliage in quantities which will not significant compared to the amount contacting the roots and other below-ground structures.

The term "crop," as used herein usually refers to plants raised in fields in an agricultural setting, and includes, along with tomatoes, grapes and other plants intended for human or animal consumption, plants intended for use as fibers, plants to be used as or processed into medicaments, plants grown for fragrance, flowers, herbs, and decorative, recreational, and ornamental plants. In this context, the term includes tree farms, such as those growing conifers to be used as Christmas trees, and grasses grown for use as turf The term can also encompass, in context, plants grown in greenhouses.

References to an "ROS/inducer mixture" mean a mixture of one or more reactive oxygen species (such as peracetic acid) and one or more plant systemic inducers.

Unless otherwise specified, references herein to "parts per million" (or "ppm") used in reference to a mixture of an ROS (which is usually in a solution with other ingredients, such as sequestering agents and surfactants) and a systemic inducer (which is also usually in a solution with chelating agents, surfactants, or other ingredients, which in preferred embodiments will contain humic acid), refers to the concentration of the solution containing the ROS component, as will be made clearer in the discussion below. The term is also used herein in reference to a mixture of an ROS (which is also usually in a solution with chelating agents, surfactants, or other ingredients, which in preferred embodiments will contain a systemic inducer) and humic acid.

Unless otherwise specified, reference herein to a particular concentration of an ROS/inducer mixture or of an ROS/humic acid mixture is of the concentration of the ROS portion of the mixture (including any additives), but implies the presence of a systemic inducer (including any additives) or of humic acid (including any additives), respectively, at a concentration about one-tenth that stated for the ROS portion of the mixture. That is, if an ROS/inducer mixture is stated to be applied at 2500 ppm, the ROS portion of the mixture (including relatively small amounts of any additives, such as surfactants, chelating agents or other ingredients noted herein) is 2500 ppm, and a systemic inducer is present at about 250 ppm (including relatively small amounts of any surfactants, chelating agents or other ingredients which may be added to the inducer). Typically, the ROS/inducer mixture will be in an aqueous solution, but in some formulations, can be applied as a mixture of dry ingredients which will be wetted after application.

The phrase "cation redox reducing agent" is any reducing agent that donates electrons to a cation that has participated in the generation of an oxygenated radical. In certain instances, the cation is oxidized back to its active species, thus acting as a "free radical pump," capable of again generating oxygenated radical species.

The phrase "divalent cation having redox potential" is any divalent cation that can accept additional electrons.

As used herein, the phrase "reducing the level of microorganism by 40%" means that there are at least 40% fewer microorganisms present in a sample of soil contacted with a composition than there are in a control sample which has not been contacted with the same composition. The number of microorganisms present can be determined by any of a number of assays known in the art, such as by plating out samples on agar plates and quantitating the resulting colonies.

The term "exogenous," with respect to the presence of a cation redox reducing agent or divalent cation having redox potential, means that the agent or divalent cation is added to a composition to raise its concentration over that which normally or naturally be present. It does not include trace amounts which might naturally be present in soil or manufactured compositions (such as humic acid, which is typically extracted from Leonardite), or which might be added as an incidental effect of normal processing. For example, minor amounts of the divalent cations manganese or copper might leach into a composition stored in a container made of those materials, but such conteminants would not be considered the addition of an exogenous divalent cation for purposes of this invention.

II. ROS/Inducer Mixtures a. Reactive Oxygen Species and Methods of Use

As noted, the method of the invention involves the use of a reactive oxygen species ("ROS") and one or more systemic inducers. A number of ROS can be used in the methods of the invention. Many ROS compounds are commercially available. In general, ROS with higher active oxygen quotients are preferred. Preferred ROS for use in the invention include, for example, peracetic acid, hydrogen peroxide, calcium peroxide, sodium percarbonate, and urea peroxide. Less preferred are sodium peroxide and magnesium hydroxide.

Peracetic acid is the ROS particularly preferred for use in the invention. It is much more stable than hydrogen peroxide and has a higher active oxygen quotient. It is also commercially available from a number of sources, including FMC Corporation (Chemical Products Group, Philadelphia. Pa.), Solvay Interox (Warrington, United Kingdom)and Degussa Corporation (Ridgefield Park, N.J.). It is desirable that the peracetic acid used be shelf-stable, although non-shelf stable acid can be used if it will be used before substantial loss of active oxygen occurs. The most commonly available form of peracetic acid is made using sulfuric acid. The use of peracetic acid made in this manner is not preferred, since any residue of sulfuric acid which may remain in the peracetic acid will be phytotoxic. Accordingly, this form of peracetic acid should not be used unless any residue of sulfuric acid has been reduced to levels which are not phytotoxic. Peracetic acid made by other methods is preferred. Peracetic acid should be handled in stainless steel or plastic approved for the purpose to reduce contamination and decomposition. Typically, the peracetic acid is mixed to a concentration of 5% (w/v).

One significant problem in using ROS is heavy metal contamination, which causes premature decomposition of the ROS and, hence, a reduction in its effectiveness. To reduce the amount of contamination by heavy metals, small amounts of chelating or sequestering agents, such as tetrapotassium pyrophosphate, can be added to sequester heavy metal ions. Since dust can blow into the mixture as it is being prepared even in applications where it would not appear that heavy metal contamination would be a problem, it is desirable that ROS used in the invention have a small amount (0.05% by weight), of tetrapotassium pyrophosphate or another chelating or sequestering agent present as a precaution. The use of polyethylene, plastic tanks, stainless steel tanks, and polyethylene, plastic, or stainless steel lines, is preferred in handling peracetic acid.

The amount of heavy metal contamination can also vary by the means of application, since some farm equipment, for example, such as metallic sprayers and irrigation equipment, can be expected to have a higher level of heavy metal contamination than, for example, a rubber hose. A higher level of chelating or sequestering agent should be used in situations where the application equipment may itself have heavy metal contamination. Conversely, many ROS start decomposing if the level of a chelating or sequestering agent reaches too high a level. To reduce this problem, higher levels of chelating or sequestering agent are added to the systemic inducer, which is not mixed with the ROS until shortly or immediately before use, so that there will not be sufficient time before application to the plants for a substantial amount of decomposition to occur, while the chelating or sequestering agent is still present to protect the ROS while it is exposed to the possible contamination. Conveniently, where the ROS and the systemic inducer are prepared well in advance of use, they are packaged in separate containers, one containing the ROS and the other the systemic inducer and the sequestering agent.

Peracetic acid is usually used in an aqueous solution of a desired concentration. Conveniently, it is made in a 5% solution, to which sequestering agents, surfactants, and other agents can be added. The calculations herein concerning concentrations of ROS or of ROS/inducer mixture were made using a 5% solution of peracetic acid solution, with the sequestering agents and other additives noted above. The solution was considered to represent 100% for purposes of calculating parts per million. Other concentrations of peracetic acid or other ROS can of course be used, with appropriate adjustment in the calculations to determine the parts per million resulting from any dilution. For example, if a 15% solution of peracetic acid is used, than only one third the amount of peracetic acid would be needed to supply the same number of parts per million. It is well within the ability of the practitioner to calculate the ROS present in parts per million for any given starting concentration.

Although peracetic acid is used in an aqueous solution, other compositions exist which form reactive oxygen species upon the addition of water. These compositions can be used, for example, to reduce transportation and handling costs associated with the ROS. Compounds useful in this regard include calcium hydroxide, sodium percarbonate, and potassium permanganate, with sodium percarbonate and potassium permanganate being less preferred. Typically, the composition is applied to a field and the field is then watered. These compounds are applied at rates which produce after watering concentrations equivalent to those discussed herein for the aqueous solutions of peracetic acid.

b. Systemic Inducers and Method of Use

A variety of systemic inducers can be used with the ROS. Preferably, the plant systemic inducer used will be either a biological inducer, such as a beneficial microbe, or a chemical systemic inducer. Biological components, such as glycoproteins, can now be routinely manufactured through recombinant techniques.

While biological inducers such as microbes can be used, it is usually more convenient to use chemicals systemic inducers, which can be synthesized in bulk at reasonable cost. Preferred systemic inducers are salicylic acid, jasmonic acid, isonicotinic acid, chitosan, beta-1,3, glucan, other mixed glucans, dichloroisonicotinic acid, Messenger™ (EDEN Bioscience Corp., Bothell, Wash.), and Actigard.™ In some embodiments, the systemic inducer can be a glucan-containing kelp, such as *Ascophyllum nodosum* and *Laminaria digitata*, or other seaweeds. Such kelps and other seaweeds are commercially available as fertilizer or plant nutrient supplements from a number of sources, such as North American Kelp (Waldoboro, Me.), Thorvin, Inc. (New Castle, Va.), American Kelp Corp. (San Diego, Calif.), Agrikelp (Colburne, Ontario, Canada), and Maxicrop USA, Inc. (Elk Grove Village, Ill.). Humic acid can also be used as a systemic inducer, or as a one component of a mixture containing at least one other systemic inducer.

One particularly preferred systemic inducer is salicylic acid. This compound is available commercially in solid form. Typically, the solid form is mixed with a base to create a salt, which is readily solubilized. While caustic soda or other high pH substances can be used, caustic potash is preferred as the base since the potassium in the caustic potash is a plant nutrient and is therefore compatible with the use of the resulting mixture as an agricultural product. After forming the salt, a small amount (~1%) of 80% phosphoric acid is added to buffer the solution since it tends to still have a high pH. Phosphoric acid should be added until the pH is reduced to about 8 (other inducers may have optimal activity at other pHs, which can be readily determined by simply applying the mixtures at different pHs to plants and then assaying for expression of SAR-related genes as taught in the Examples). Small amounts (2.5%) of surfactants may also be added to help absorption of the mixture by plant roots, leaves, and other plant surfaces. Surfactants are commonly used as wetting agents; commercially available agents suitable for use in the invention include Triton H-66™ and Tergitol 15 S.™ In a preferred embodiment, 2.5% of each of these surfactants is added to the systemic inducer mixture. Other surfactants can be used. The surfactants should be selected for compatibility with peracetic acid or the particular ROS which will be employed. For example, one can determine the active oxygen quotient of the ROS by industry standard methods, proceed to mix the ROS with the desired surfactant, and retest the active oxygen quotient. A loss of more than 1% is generally considered to mean the two agents are incompatible.

In some embodiments, two or more systemic inducers may be administered to increase the robustness of the response. Typically, the total concentration of the inducer portion of the ROS/inducer mixture will remain the same, but will be divided between or among the inducers selected for the application in question.

In preferred embodiments, humic acid is added to be 0.1% to 50% of the total systemic inducer present, although humic acid can also be used as the major species of inducer present, constituting more than 50% of the total systemic inducer present, and can if desired be the only systemic inducer used. We have found particularly good results mixing salicylic acid and humic acid in a 1:1 ratio and adding this mixture to the ROS to form the ROS/systemic inducer mixture. It should be noted that the standard grade of humic acid has a solubility of 12%, but higher percentages of solubility may be possible for some formulations. The percentages stated for humic acid as a component of a systemic inducer mixture are for a 12% solution, and the percentages can be adjusted as appropriate if the solution used is of a higher or lower percentage.

In the most preferred embodiment, the systemic inducer is administered at about one-tenth the concentration of the ROS. Conveniently, the systemic inducer is mixed in a 10% solution. The ROS and chemical inducer can then be applied at equal volumes to maintain the desired 10 to 1 proportion. For example, one gallon of the ROS solution (such as the 5% solution of peracetic acid noted in the preceding section as considered to be a 100% solution for purposes of these calculations) can be mixed in a tank with one gallon of the 10% systemic inducer solution. The resulting mixture can then be diluted to any desired level of parts per million. It should be noted again that for purposes of calculating parts per million, we consider only the ROS solution component. The parts per million of the systemic inducer portion is implied at about 10% of the concentration of the ROS, but is not separately calculated or considered in the ppm calculation. Thus, a calculation of "2500 ppm" refers only to the ROS component (with all of its surfactants and the like), without including the 250 ppm of systemic inducer which would be added by the systemic inducer portion of the ROS/systemic inducer mixture.

Beneficial microbes can also be used as systemic inducers. A number of microbes are known to act as systemic inducers, and usually, the microbe chosen is not pathogenic to the plant to which it is to be applied; for example, it may be avirulent or a microbe to which the plant in question is resistant, or, preferably, a saprophyte. E.g., Kiessig and Malamy, supra, at 1440. Preferably, the microbe should be nonpathogenic to the plant and one which improves the plant's growth, yield and quality. For example, species of bacteria such as Bacillus, Serratia, and Pseudomonas and fungi such as Trichoderma are known to act as systemic inducers. It should be noted, however, that the effects of any particular bacterial species can vary by soil type, the time of year, and the particular crop to which the organism is to be applied. Accordingly, the practitioner will usually first test the organism on the crop in a small field to ascertain whether a particular microbe is beneficial to the crop in question, and will examine the growth, yield and quality against a non-treated or mock-treated crop, until he has identified organisms beneficial in his fields, on the crop in question.

Microbial inducers are usually applied live at between around $10^3$ and $10^{10}$ colony forming units (CFU) per milliliter. The microbial inducers can be applied by spray or by irrigation. Typically, between about ¼ gallon and 75 gallons of microbial inducer at this concentration is applied per acre. The microbial inducer can be applied in any convenient amount of water so long as the desired amount of microbial inducer (for example, 5 gallons of microbial inducer culture of between about $10^3$ and $10^{10}$ CFU per ml) is applied. In a more preferred embodiment, about ½ gallon to about 50 gallons per acre is applied, and in a still more preferred embodiment, about ¾ gallon to about 25 gallons per acre is applied. Even more preferred, about ¾ gallon to about 10 gallons is applied per acre. In the most preferred embodiment, about 1 gallon to about 5 gallons are applied per acre.

c. Administration of ROS and Inducers

Usually, the ROS and a chemical systemic inducer will be administered within 36 hours of one another. More preferably, the ROS will be administered within 24 hours of administration of the systemic inducer. Even more preferably, the ROS will be administered within 12 hours or less of administration of the systemic inducer. Still more preferably, the ROS and a chemical systemic inducer will be administered within about an hour of each other. Most preferably, the two agents will be applied together as a mixture in an aqueous solution. The methods of the invention do not contemplate the injection of the ROS or of the systemic inducer into individual plants or leaves, nor the administration of gaseous ozone.

If a microbial inducer is to be used, the method is practiced by administering one or more ROS within about 2 to about 36 hours (preferably, about 12–24 hours) of administration of the microbial inducer of SAR. The microbes are not applied at or about the same time as the ROS since an ROS such as hydrogen peroxide would tend to kill the microbes and might decrease the desired effect. It should be noted that since kelp and other seaweeds are used in dried form or as liquid extracts, there is no concern that the ROS would kill them. Accordingly, they are generally used following the guidelines for chemical systemic inducers even though they are plants.

An ROS-chemical inducer mixture can be mixed up to a week before use, preferably within 24 hours of intended use, and more preferably within 4 hours of intended use. Most preferably, the mixture is made immediately before use, because the ROS tends to decompose once mixed. Typically, the ROS and inducer will be mixed at concentrations where each one can independently in a range between 1 ppm and about 100,000 ppm. More preferably, the range is about 50 ppm to about 50,000 ppm. (Applications below 100 ppm will typically be used only where longer periods of application are contemplated.) Still more preferably, the range is about 100 to about 25,000 ppm. Even more preferably, the range is about 100 and about 10,000 ppm.

While the range of either component can vary, in general, it is preferred that the systemic inducer be applied in a range from about equal to about one-twentieth the concentration of the ROS. In more preferred embodiments, the systemic inducer is applied at concentrations lower than the ROS. In a most preferred embodiment, the systemic inducer is present at about one-tenth the concentration of the ROS in ppm.

In the most preferred embodiment, the ROS concentration is between about 500 and 5,000 ppm, and the systemic inducer concentration is about 50 to about 500 ppm, that is, the inducer is applied at about one-tenth the concentration of the ROS. As noted in the previous section, since the inducer is typically mixed in a 10% solution, an aqueous solution of the inducer can conveniently be mixed in equal volumes with an aqueous mixture of the ROS to achieve the desired ratio between the two.

Generally, we anticipate that cost and other considerations will lead the practitioner to apply the chemicals at concentrations within this range. In some instances, a practitioner may, however, desire to apply the compounds at a higher concentration. There is an upper limit on the concentration of ROS which can be applied to a plant without toxicity, and the upper limit varies for different types of plants. Citrus plants, for example, can tolerate relatively high levels of ROS. The upper limit on the concentration of the ROS for any particular plant type can be routinely determined by any of several methods known in the art, such as exposing sample plants of the type in question to various concentrations of ROS and examining the plants for signs of stress, such as browning of tips of leaves, indicating that the concentration at which the stress signs occurred is too high for that type of plant. Upper limits on the concentration of systemic inducer can be determined in the same manner.

It should be noted that with regard to soil applications, the compositions and methods of the invention are preferably prepared, applied, or both, without exogenously added divalent cations. Additionally, in soil applications, the compositions and methods of the invention are preferably prepared, applied, or both, without exogenously added cation redox reducing agents. For foliar applications, the presence of divalent cations or of cation redox reducing agents is permissible, but the compositions and methods can be prepared or applied without these agents if desired.

IV. Application of the Agents of the Invention a. Foliar Application

The application of substances to the foliage, or aboveground portions of plants, is known as foliar application. Foliar application has been performed on farms, in greenhouses, on flowers, and in other agricultural settings for decades, and is performed in any of a variety of ways known in the art. For example, farmers routinely apply pesticides and other agents to their crops by means of tractor mounted sprayers, by crop dusting, through pressurized sprinklers, and through systems such as elevated hoses used to spray grapevines.

Typically, the ROS/inducer mixture is dissolved or diluted in water, as appropriate, before use. For foliar application, it is preferred to apply the ROS/inducer mixture at a concentration between 1 ppm and about 100,000 ppm. More preferred is a range of about 50 to about 50,000 ppm. Even more preferred is a range of concentration between about 1000 and about 7000 ppm. Particularly preferred is a range between about 1,750 ppm and about 5,000 ppm. In a more preferred embodiment, the concentration is about 3,500 ppm. Most preferred is a concentration about 2,500 ppm. (As noted earlier, all of these concentrations refer to the ROS component only, with the systemic inducer content, preferably at about 10% of that of the ROS, being implied. Thus, the most preferred concentration set forth in this paragraph is the concentration of the ROS component, with the presence of about 250 ppm of systemic inducer being implied.)

We have found that a concentration of about 2,500 ppm is high enough to be effective, but provides a margin of safety for mathematical errors in applying the invention in practice. Since farmers have been accustomed for years to mixing pesticides, fertilizers, and other agricultural chemicals for use in their fields, the mixing and application of an ROS/inducer mixture is well within a farmer's skill. Nonetheless, errors can occur. The preferred concentration of 2,500 ppm is such that if the farmer accidentally halves the concentration (to 1,250 ppm), it will still be high enough to be effective, while if it is accidentally doubled (to 5,000 ppm), it will not be high enough to be toxic to the plants. Lower or higher concentrations can, of course, be employed, at the user's option, within the limits noted in preceding sections.

The amount of the mixture to be applied to the fields will depend on several variables. In foliar application, the goal is to moisten the foliage. How much water is necessary to accomplish this will depend largely on the amount of foliage to be covered and the precision of the method of application in directing the mixture to the foliage without also wetting the surrounding area. The amount of foliage will depend, for example, on the amount of age of the plants (young plants typically have smaller leaves than mature plants), the type of plant (different types of plants differ in the amount and density of their foliage) and the health of the plants. Farmers have, of course, applied various chemicals to their crops for years, and are well familiar with judging the amount of liquid needed for foliar application on crops of different ages and types. Once the amount of liquid to be used is determined, the amount of ROS/inducer mixture to be added to achieve any desired concentration in parts per million is readily determined. The determination of whether the rate of application is sufficient to moisten the foliage is also easily made and the amount readily adjusted until a satisfactory rate is achieved.

It should be noted that some systems, such as sprinkler systems, spray the whole plant while they water the soil. In the art, and as used herein, such methods are considered soil applications since their purpose is to soak the ground and not merely to wet the leaves or other portions above the ground.

As a guide to the practitioner, the table below sets forth foliar applications which were found particularly useful for certain crops in field trials conducted in Mexico. It is anticipated that optimization of rates of application and volumes of spray water will be necessary for crops raised under different conditions of temperature and moisture.

TABLE 1

Preferred foliar applications for different crops.

| Crop | Spray Water Gallons per Acre | Rate - Ounces/ Acre | Application Frequency |
| --- | --- | --- | --- |
| Lettuce, Crucifers, Asparagus, Garlic, and Carrots | 10–50* | 8–16 | Apply starting at germination at an interval of 10 days or less according to conditions.** |
| Tomato, Chile, Melon, Cucumber, Potatoes | 10–80 | 8–26 | Apply starting at germination at an interval of 14 days or less according to conditions. |
| Citrus | 200–400 | 64–96 | Apply during first root flush. If necessary repeat in 30 days. |

TABLE 1-continued

Preferred foliar applications for different crops.

| Crop | Spray Water Gallons per Acre | Rate - Ounces/ Acre | Application Frequency |
|---|---|---|---|
| Wine, Raisin, & Table Grapes | 50–200 | 16–64 | Apply every 14 days. Under adverse conditions apply every 7 to 10 days. |

Legend for Table 1.
*/ The spray application depends on the amount of leaf surface area. The first number set forth for each crop type or group of crop types is for young plants, the second is for more mature plants with larger leaf areas. The practitioner can determine when to switch to higher water volume by determining when the lower volume becomes insufficient to wet the entire leaf surface of the plant.
**/ The "conditions" are the degree of pathogen pressure on the crops. For example, if downy mildew is seen on a lettuce crop, the interval before the next application will be decreased by a day. If downy mildew is still observed, the interval for the next application will be decreased by a day, and so on.

b. Soil Application

In soil application, the soil is preferably first saturated to wet the particles of the soil so that the ROS/inducer mixture can move freely in the soil and reach the roots of the plants. Therefore, preferably the soil is saturated to 70–80% field capacity with ordinary water prior to ROS/inducer application. The ROS/inducer mixture is then applied at a concentration of between 1 and about 100,000 ppm. Typically, the concentration will be between about 500 ppm and about 10,000 ppm, preferably at a concentration of about 750 ppm to about 7,500 ppm, and more preferably at a concentration of about 800 ppm to about 5,000 ppm. The particular concentration to be chosen varies primarily according to the flow rate of water permitted by the method of application. Methods having a higher flow rate generally require a lower concentration of ROS/inducer mixture, perhaps because more water containing the mixture reaches the roots of the plants. Conversely, lower flow rates will generally require higher concentrations of ROS/inducer mixture. Alternatively, the time of the application of the mixture can be altered. Thus, use of a low flow rate and low concentration of mixture can be balanced by increasing the time in which the water containing the mixture is applied. Thus, halving the flow rate or concentration of mixture can be compensated for by doubling the application time of the water-mixture solution. While flow rate is a particularly important variable, the crop to which the mixture is being applied may also help determine the concentration of mixture to be applied. Typically, perennials take higher concentrations than do annuals.

It should be noted that the farmer is usually well aware of the flow rate per acre of the irrigation or other soil application system in place on his or her property, as well as the acreage to be covered. The farmer can calculate the amount of water which will be used in watering the land for any particular amount of time (for example, 300 gallons per minute times 50 acres times 30 minutes is 450,000 gallons of water). The farmer can then calculate how much ROS/inducer mixture is needed to result in an application of the desired concentration of the mixture.

The ROS/inducer mixture is applied for a period of time, typically ranging from about two minutes to about an hour. In some cases, the practitioner may want to apply the mixture at a lower concentration, but for a longer period, such as overnight or over several days. Such applications are within the purview of the invention, so long as they result in increases in PR proteins, PAL, or HPRG, or of disease resistance. The time of the application will also vary according to the particular method employed. For drip systems, the mixture is applied for about 5 minutes to about 45 minutes. More preferably, the mixture is applied for about 9 minutes to about 30 minutes. Even more preferably, the mixture is applied for about 15 to about 25 minutes. Consistently good results have been achieved in our tests when the mixture is applied for about 20 minutes. Accordingly, that period of application is the most preferred.

The practitioner will appreciate that different systems of application have different flow rates. For example, overhead sprinklers generally have relatively higher flow rates than do drip systems, and the preferred application time is correspondingly less: from about 4 minutes to about 10 minutes. Microsprinkler systems such as Fan Jet™ typically have flow rates between that of drip systems and that of sprinklers, and accordingly have application times somewhat higher than that of sprinklers, with about 10 to about 15 minutes being preferred.

The ROS/inducer mixtures are typically applied to the soil by being run through a hose, pipe, drip, sprinkler, irrigation channel, or other mechanism. In practice, the devices used are not necessarily precision equipment. Accordingly, when the water flow is turned off, water will typically continue to drip or run from the hose or through the irrigation channel or other applicator for some time. It is therefore understood that the times of application will generally be an approximation and will be measured from the start of the flow of the mixture to when the flow of the mixture is turned off, whether or not some of the mixture continues to drip or run from the applicator.

Following application of the ROS/inducer mixture as set forth above, the mixture will typically be in the top few inches of soil. For many plants, the root system is deeper in the soil. It is therefore desirable to help move the mixture 6 to 12 inches into the soil to reach the root structures involved in active uptake. To achieve this, it is desirable to use a "water push" to create a concentration gradient after application of the ROS/inducer mixture. This is achieved by following the application of the ROS/inducer mixture with an application of water. The water application can be as short as a few minutes or as long as several hours. Preferably, however, the water application is between about 30 minutes and about one and one half-hours and more preferably is about one hour. Such "water pushes" to create concentration gradients are commonly used by farmers in applying agricultural chemicals and are accordingly well known in the art.

In soil applications, the ROS/inducer mixture is used without cation redox reducing agents or divalent cations having redox potential in amounts sufficient to reduce the levels of living microorganisms in soil around the roots of the plants (in combination with the ROS and inducer mixture) by 40% or more. The levels of microorganisms in soil can be readily determined by techniques well known in the art. For example, soil dilution plating assays can be performed by taking a gram of soil, suspending it in 10 mls of sterile water, making a serial dilution and plating each dilution onto a suitable growth medium. This will determine culturable colony counts in the soil sample. In this instance, one would perform this assay on two soil samples with similar microorganisms and levels of those microorganisms and comparing the level of the living microorganisms remaining in the treated sample against the level of the living microorganisms in the untreated (control) sample.

V. Uses of the Invention

The invention can be used to protect almost any plant capable of responding to pathogenic attack with systemic acquired resistance. Assays for determining whether a particular type of plant can benefit from the induction of systemic acquired resistance by means of the invention are well known in the art. For example, Pnorthern blots can be performed to determine whether transcription of genes for PAL, HRGPs, chalcone synthase, peroxidase, or pathogenesis-related proteins have been upregulated in response to treatment with a ROS/inducer mixture. Exemplar assays are taught in the Examples.

The plants to be protected by means of the invention can be dicots, such as carrots, lettuce, tomatoes, grapes, citrus fruits, and beans, or monocots, such as corn. The plants can be grown for human or animal consumption, such as grains, vegetables, and fruits, can be intended for decorative use, such as flowers, or can be intended for ornamental use, such as trees grown for use as Christmas trees or plants intended for use as house plants. Further, they can be plants grown for fiber, such as cotton plants, for use as turf, for example on golf courses, lawns or ballfields, or for use as or in medicaments. Most commonly, the invention will be used to protect plants grown in fields as crops or in other open conditions, such as tree farms or turf; the invention can, however, also be used to protect plants grown in settings such as greenhouses and hothouses.

The invention can be used to protect plants against any pathogen against which systemic acquired resistance can be generated. Pathogens against which SAR can be raised include a variety of bacteria and viruses, a number of fungi, nematodes, Phylloxera, and even aphids. The Examples demonstrate the use of the invention to protect crops in the field against several pathogens, including insects, fungi and nematodes.

Because the invention protects crops against at least a portion of the damage which would otherwise be caused by these pests, a higher percentage of the crops grown for human consumption can be sold as first quality crops. Moreover, since less of the crop is unmarketable, the invention results in a higher yield per acre. These factors combine to result in higher revenues per acre for the farmer.

VI. Methods for Determining if PAL, HPRG, Peroxidase Chalcone Synthase, Pathogenesis-related Proteins, or Their Transcripts are Increased A number of methods are available to determine if PAL, HPRG, peroxidase, chalcone synthase, pathogenesis-related proteins, or their transcripts, or other enzymes or proteins of interest are increased. One can, for example, detect an increase in RNA levels in response to a ROS/inducer mixture in comparison to a control by means of assays such as northern blots. Exemplar northern blot assays are discussed in the Examples, below. Alternatively, a protein, such as a HRGP, can be used to raise antibodies against the protein by injecting it into mice or rabbits following standard protocols, such as those taught in Harlow and Lane, *Antibodies, A Laboratory Manual* (Cold Spring Harbor Laboratory, Cold Spring Harbor, N.Y., 1988). The antibodies so raised can then be used to detect the presence and amount of the protein in a variety of immunological assays, such as ELISAs, fluorescent immunoassays, and Western blots.

EXAMPLES

The following examples are provided by way of illustration only and not by way of limitation. Those of skill will readily recognize a variety of noncritical paramfeters which could be changed or modified to yield essentially similar results.

Example 1

Preparation of ROS and Systemic Inducer and Creating an ROS/inducer Mixture

This example demonstrates the making of preferred forms of ROS and systemic inducer for forming compositions of the invention and for use in the methods of the invention. In the procedures set forth, normal protocols for preparing the ROS and the systemic inducer have been altered to include amounts of chelating agents, sequestering agents, and surfactants our work has indicated render the final ROS/inducer mixture the most effective.

Making peracetic acid ("PAA") for use in the invention commences with a decision as to the amount of PAA desired, for example, 1 gallon or 100 gallons. The PAA is then made by blending the following ingredients, in the order shown. We prefer to use a 5% solution of PAA. At a 5% solution, PAA weighs 9.4 pounds per gallon, and it is therefore possible to calculate the weight of any desired amount of PAA (for example, 10 gallons would equal 94 pounds). The percentages below denote the weight of the ingredient to add, in percent of the final weight of the final amount of PAA desired. Following the recipe below, for example, to mix ten gallons of PAA, one would use 47 pounds (50% of 94) of 50% hydrogen peroxide. The recipe is as follows:

25% De-ionized water

50% 50% Hydrogen peroxide

11% Glacial acetic acid 0.05% Tetrapotassium pyrophosphate 0.05% Versonex 80™ (a chelating agent; other commercially available chelating agents can be substituted)

This mix is then brought up to final weight with 13.9% de-ionized water. Similar calculations can be made to mix solutions of PAA at different concentrations, if desired.

For making a solution of salicylic acid, a preferred inducer of systemic resistance, the following means is preferred. As in the method above, one first decides the total amount of the product desired and calculates the weight of that amount. To make the 10% solution of salicylic acid and humic acid which is the preferred embodiment (a 10% solution of salicylic acid weighs 9.5 pounds per gallon), the ingredients are mixed according to the following recipe, by percentage of the final weight of the mixture:

30% De-ionized water

10% Salicylic acid

10% Humic acid (in the form of a 12% aqueous solution)

10% Caustic potash

1% 80% Phosphoric acid 2.5% Tergitol 15 S 9™

2.5% Triton H-66™

1% Versonex 80™

12% Tetrapotassium pyrophosphate

This mix is then brought up to final weight with 21% deionized water. As noted, this recipe results in a 10% solution of systemic inducer. The solution can then be mixed in an equal volume with an ROS, such as the 5% peracetic mixture described above, to obtain a mixture with concentrations in the preferred ratio of 10:1 ROS to systemic inducer. In the Examples below, humic acid in an aqueous solution was substituted for one quarter of the deionized water so that it constituted 10% of the final weight of the salicylic acid solution.

The Examples below include laboratory and field trials of the invention. In the laboratory trials, some plants were contacted with ROS mixture without also being contacted with systemic inducer mixture. Where the systemic inducer mixture was added, it was added at 200 ppm. References to concentrations of the inducer refer to the concentration of the mixture, with the surfactants and other agents noted above.

In the field trials, the concentrations stated are of the ROS portion of the mixture. In each field trial, an equal volume of the systemic inducer mixture was added so that the inducer mixture was present at about one-tenth the concentration of the ROS mixture.

Example 2

Induction of Expression of the PR-1a Gene

This example shows that plants sprayed with an ROS/inducer mixture in a laboratory showed greater expression of the gene encoding the pathogenesis-related protein PR-1a than did plants sprayed with either an ROS alone or with a systemic inducer alone.

Fourteen-day old red kidney bean plants (*Phaseolus vulgaris*) were sprayed from an overhead boom until the leaves were wet and spray began to run off them. Plants were treated with one of the following treatments: water, the ROS, peracetic acid, at a concentration of 3,500 ppm, peracetic acid at a concentration of 10,000 ppm, a ROS/ inducer mixture, at 3,500 ppm of the ROS and 200 ppm of the inducer (salicylic acid) mixture, of the same mixture at 10,000 ppm for the ROS and 200 ppm of the inducer, and of just the inducer, at 200 ppm.

The plants were then left for 24 hours, after which the leaves were subjected to extraction of their total RNA by the procedure described in Logemann, J., et al, "Improved method for the isolation of RNA from plant tissues." Anal Biochem. 163:16–20 (1987). Formaldehyde gels were then prepared, loaded with 10 µg of the total RNA, and run to separate RNA by size, according to standard methods (Sambrook, J., et al., Molecular Cloning, A Laboratory Manual. Cold Spring Harbor Laboratory Press, Cold Spring Harbor, N.Y. (2nd ed. 1989)). The gels were then blotted (as described in Sambrook, supra), and hybridized to a probe for PR-1a prepared according to the method described in Zdor, R., and A. J. Anderson, "Influence of root colonizing pseudomonads on defense mechanisms of bean." Plant and Soil. 140:99–107 (1992). Nonradioactive probe was prepared via random priming of only the cloned insert. Hybridization was observed and analyzed by chemiluminescent detection of the bound probes using the "Genius System," (Boehringer Mannheim Corporation, Indianapolis, Ind.), following the manufacturer's directions. Equal loading of the RNA was judged by ethidium bromide staining of the ribosomal RNA bands.

Figure 1:
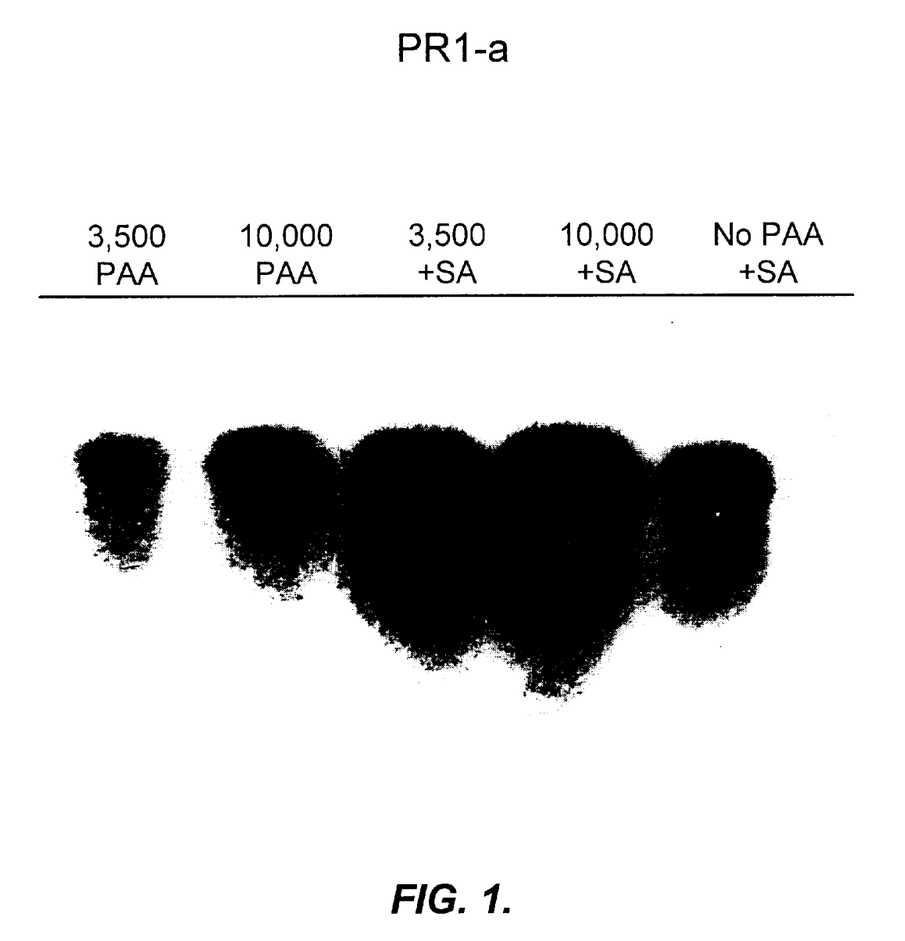

The results are shown in FIG. 1, which is a northern blot of RNA probed for PR-1a. While no water-only control was run in this northern, our previous work has demonstrated that no RNA message is detectable for plants treated only with water. PR-1a gene RNA expression increased upon treatment with 3,500 ppm of peracetic acid (lane 1) and higher amounts are seen at treatment with 10,000 ppm of peracetic acid (lane 2). The systemic inducer mixture, at 200 ppm, also showed increases of RNA accumulation (lane 5). The ROS/inducer mixture treatment, at both 3,500 ppm of ROS and 200 ppm of salicylic acid (lane 3) and of 10,000 ppm of ROS and 200 ppm of inducer mixture (lane 4), showed dramatic, synergistic effect, reflecting an effect clearly greater than a simple additive effect of the increase in RNA transcript accumulation caused by either of the two agents alone.

Example 3

Induction of the Gene Encoding Phenylalanine Ammonia Lyase

This example shows that the use of a ROS/inducer mixture causes an increase in transcription of a gene encoding phenylalanine ammonia lyase ("PAL"), another marker for plant resistance.

Bean plants were grown and treated in the same manner as in the previous Example, except that a water-only control was run, but not a test of systemic inducer without PAA. Total RNA was extracted and gels were loaded, run, and analyzed following the procedures discussed in previous Example, with the exception that no lane was run containing RNA from plants sprayed with a systemic inducer without an ROS present. Probe for PAL mRNA transcripts was prepared following the procedures set forth in Blee, K. A., and Anderson, A. J. "Defense-related transcript accumulation in *Phaseolus vulgaris* L. colonized by the arbuscular mycorrhizal fungus *Glomus intraradices* Schenck & Smith." Plant Physiol. 110: 675–688 (1996).

Figure 2:
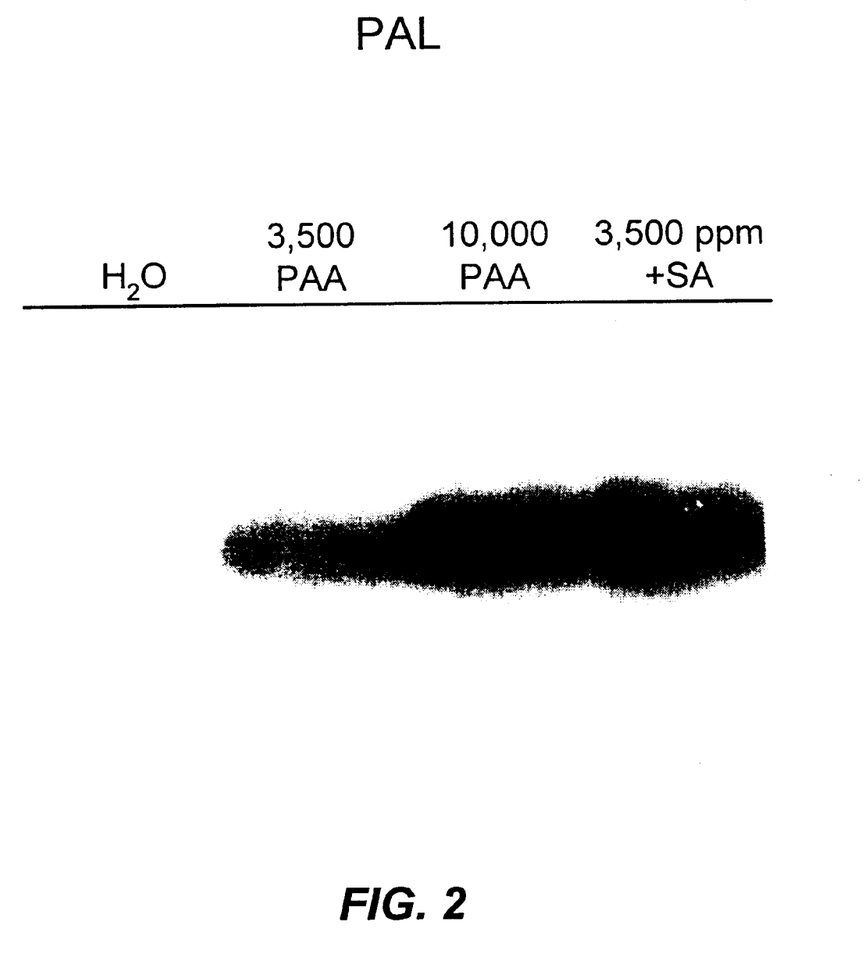

The northern blot resulting from this study is set forth as FIG. 2. No hybridizing RNA can be seen in the lane for the RNA from the water-treated controls (lane 1). The lanes for treatment with peracetic acid at 3,500 ppm (lane 2) and at 10,000 ppm (lane 3) show an increase in mRNA for PAL genes over that of the water control, with the lane for 10,000 ppm treatment showing a substantial increase in the amount of RNA compared to the lane for treatment with 3,500 ppm of PAA. The fourth lane shows that treatment with 3,500 ppm of the ROS peracetic acid in combination with an inducer mixture (at 200 ppm) resulted in levels of PAL induction at least equal to that of application of 10,000 ppm of peracetic acid in the absence of an inducer.

Example 4

Induction of Gene(s) Encoding Hydroxyproline-rich Glycoprotein by an ROS/inducer Mixture Hydroxyproline-rich glycoproteins ("HPRG" or "HYP") are known to be deposited in increased amounts in plant cell walls when plants are challenged by pathogens, and are thought to strengthen the cell walls. This Example shows that there is an increase in the level of RNA for HYP upon treatment with a ROS/inducer mixture, and that the increase was larger than that seen upon treatment with a ROS alone or with a systemic inducer alone.

Bean plants were grown and treated as in Example 2. Total RNA was extracted and gels were loaded, run, and analyzed following the procedures discussed in Example 2. Probes for HYP were prepared following the procedures set forth in Blee and Anderson, supra.

Figure 3:
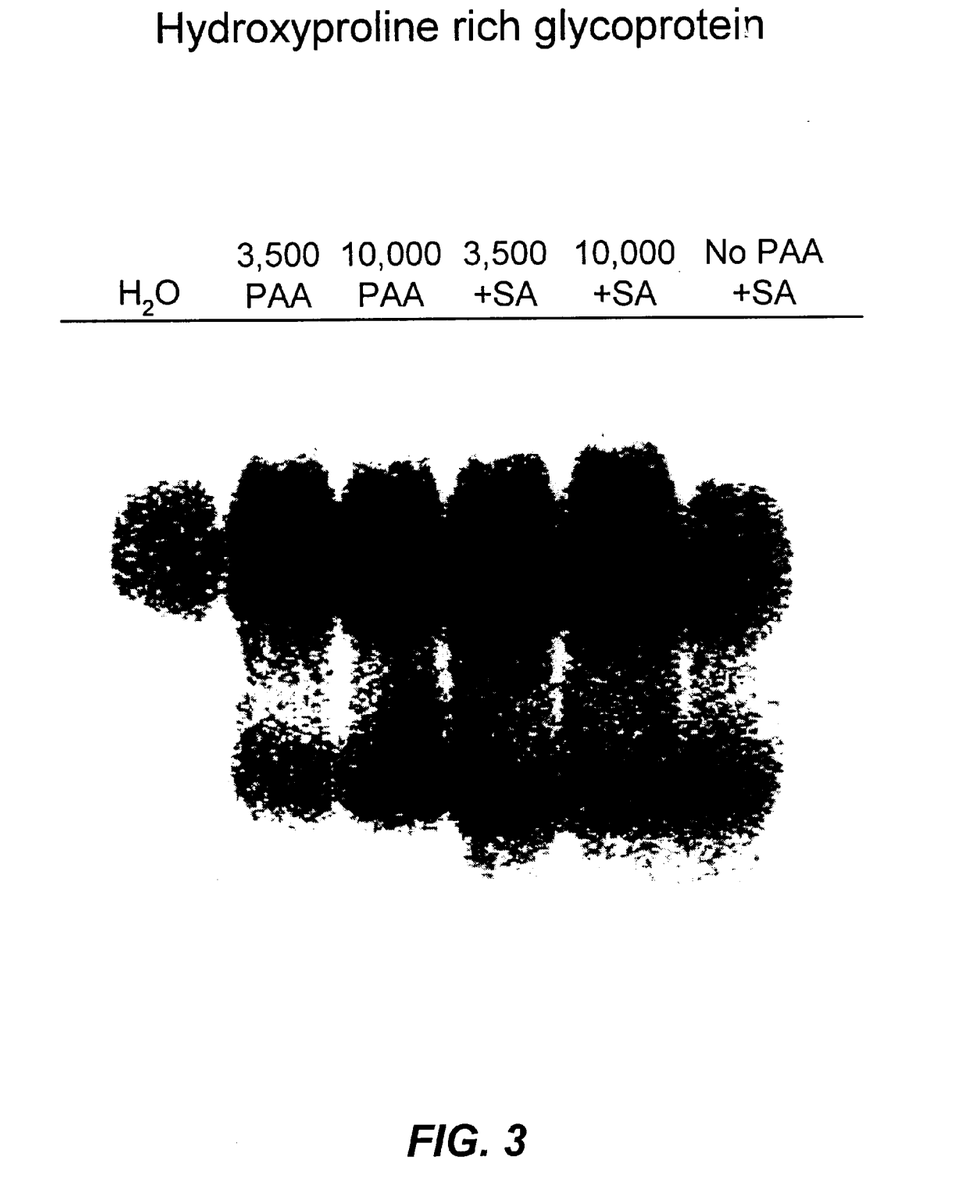

The northern blot resulting from this study is set forth as FIG. 3. The lanes for treatment with peracetic acid at 3,500 ppm (lane 2) and 10,000 ppm (lane 3) show an increase in RNA levels from HYP genes over that of the water control (lane 1), with the lane for treatment with 10,000 ppm showing substantially more hybridizing RNA than does the lane for treatment with 3,500 ppm (compare lane 3 to lane 2). Lane 6, which shows probing of RNA from plants treated with a systemic inducer (salicylic acid, at 200 ppm) but without an ROS present, shows a level of HYP induction somewhat greater than that of the lane reflecting treatment with an ROS at 3,500 ppm (lane 2) but less than that of the lane reflecting treatment with an ROS at 10,000 ppm (lane 3). Lane 4, containing RNA from plants treated with both an ROS at 3,500 ppm and a systemic inducer mixture (according to the recipe set forth in Example 1) at 200 ppm, shows a much greater level of RNA induction than is true for plants treated only with 3,500 ppm of the ROS (lane 2), and indeed is greater than the induction seen for 10,000 ppm of ROS alone (lane 3). Lane 5, reflecting treatment with an ROS at 10,000 and the systemic inducer mixture (at 200 ppm) also shows a very strong induction of HYP mRNA in comparison to the lanes reflecting application of an ROS at the same concentration (lane 5) or of the systemic inducer mixture (at 200 ppm) alone (lane 6).

Example 5

Field Trial of ROS/Inducer Mixture to Treat Nematode Infestation in Table Grapes Field trials were designed by University of California extension agents, who were instructed to design them to the same standards as for University of California experiments. This trial shows use of the invention to treat a nematode infestation in table grapes. Nematodes present in high concentrations were Ring, Citrus (Tylenchulus), Dagger (Xiphinema), Stubby Root (Trichodorus), and Lesion (Pratylenchus).

A ROS/inducer mixture of peracetic acid and salicylic acid, with surfactants, sequestering agents, and caustic potash present in small amounts (in this and in the remaining examples referred to as a "PAA/inducer mixture"), as described above, was applied to a crop of table grapes. Three applications were made, starting early in the growing season. For the first application, 1 gallon per acre of the PAA and 1 gallon per acre of the 10% inducer mixture were applied, followed by a second application 21 days later at a rate of ½ gallon of each per acre, followed by a third application 21 days after that, at the same rate as the second. Application was in water, made by drip irrigation for 30 minutes, at a flow rate of 9 gallons per acre per minute, to a final concentration of 1900 ppm, followed by a "water push." The trial was randomized, with six replicates per treatment, and 140 samples were taken from each replicate. The control was treatment with water only.

Results: Of the fields treated with water only, the yield (in number of 21 pound boxes of fruit) was: 373 boxes of No. 1 quality grapes and 282 boxes of No. 2 quality grapes, for a total yield of 656 boxes. Fields treated with the ROS/inducer mixture yielded 414 boxes of No. 1 fruit and 373 boxes of No. 2 fruit, for a total of 787 boxes. At $10 per box, the difference in yield increased revenue by $1310 per acre.

Example 6

Field Trial of the Invention Testing Ability to Reduce Powdery Mildew on Table Grapes This Example shows the ability of the invention to reduce the percentage of table grapes infected with powdery mildew, a fungal infection.

In this Example, the plants were examined to determine the number with Level 1 mildew (fewer than 3 grapes per plant with active mildew) before and post-treatment with a PAA/inducer mixture. A 50 acre vineyard was divided into 16 replicates of 88 vines each, for a total of 1408 vines in the trial. The vines in each replicate were examined, and the percentage with Level 1 powdery mildew determined. The field was then treated in mid-summer with a single, foliar application of PAA/inducer mixture by an air blast sprayer at a concentration of 1250 ppm, applied as 1 quart of mixture in 200 gallons of water. The replicates were then examined after 1 week and the percentage with Level 1 mildew determined.

Figure 4:
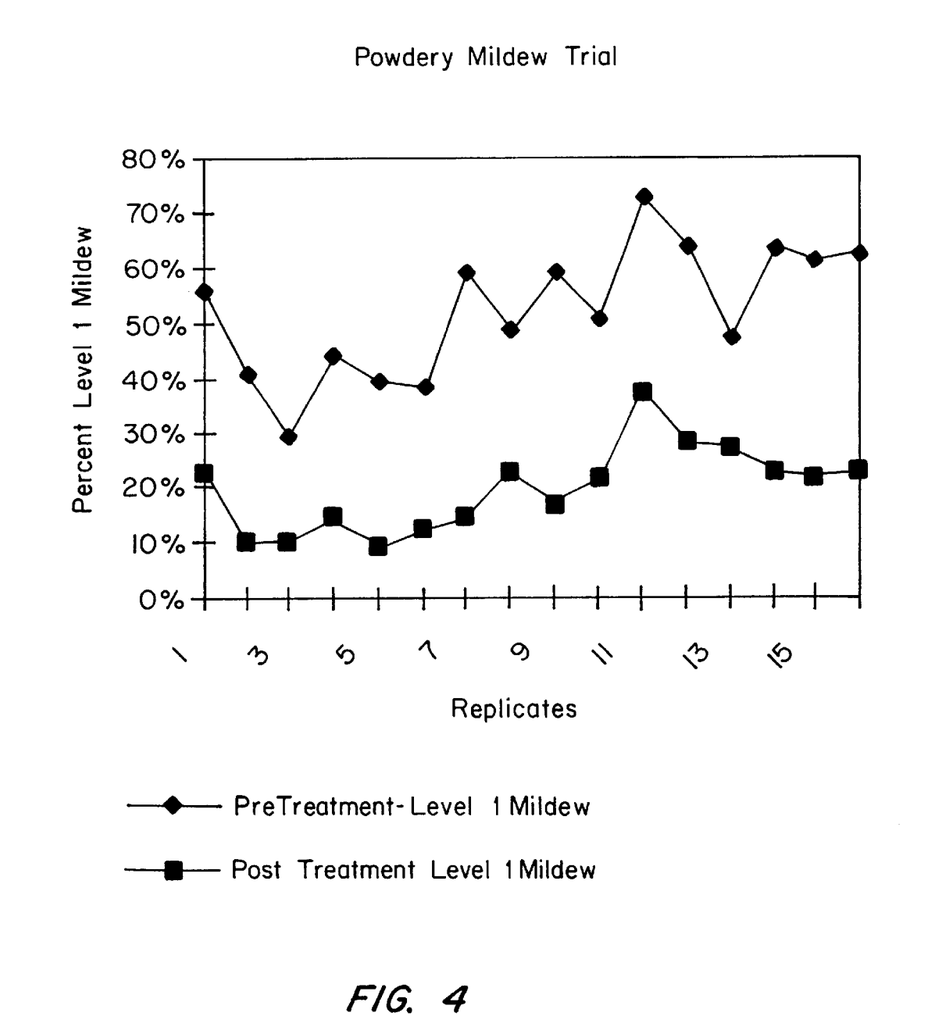
FIG. 4 is a chart setting forth the results of a field trial of the effect of applying a ROS/inducer mixture on levels of powdery mildew infection of seedless table grapes. Plants were sprayed with an air blast sprayer with 200 gallons of water at a rate of 32 ounces per acre. The spray contained a mixture of PAA at a concentration of 1250 ppm and inducer mixture at a concentration of 125 ppm. Each replicate contained 88 plants, and a total of 16 replicates were treated. Level 1 mildew indicates that fewer than 3 young grapes (called "berries") per plant are infected with mildew. Diamonds: Percentage of plants in each replicate with Level 1 mildew prior to treatment. Squares: Percentage of plants in each replicate with Level 1 mildew following treatment.

The results are shown in FIG. 4. For every replicate, the percentage of plants with Level 1 mildew was markedly lower than the percentage of plants with mildew for the same replicate prior to treatment.

Example 7

Two Field Trials of the Invention Testing Ability to Reduce Pythium and Nematode Damage to Carrots This Example sets forth two field trials which together show the ability of the method of the invention to increase yield of carrots and to reduce the amount of Pythium and nematode damage to carrots compared to one of the most widely used conventional agents. Pythium, a fungus which attacks through the root system, and nematodes, which strike at the growing tip of the carrot during the first 20 days of growth, cause the carrot to split into a fork around the damaged tissue. Carrots so damaged cannot be sold as first quality, i.e., fresh carrots for eating, for which the farmer receives the highest price.

a. Field Trial A

This trial was conducted to determine yield information. Tests were of side-by-side comparisons of two 50-acre plots, with six replicates each. Carrots being treated with the PAA/inducer mixture were given a "germ water" application (in which a seed planted in fairly dry soil is given its first watering, to encourage its germination, with the treated water) by irrigation with a pressurized sprinkler system at an application rate of 1.25 gallons of mixture per acre, for a concentration of 1100 ppm. The carrots were then treated with two additional applications, one ten days after the first application and another ten days after that, at a rate of 1 gallon per acre.

To test the efficacy of the invention against currently used conventional agents, a second group of carrots were grown using a widely-used soil fumigant, Vapam™ (generically, metam-sodium), to control pests. This agent is applied to the soil as a liquid, which then emits carbon disulfide gas. Since the gas kills most living things with which it comes in contact in high concentrations, including growing plants, it is applied before the field is planted. It was applied in accordance with the label directions.

Results: Of the carrots treated with the ROS/inducer mixture, 98.2% of the carrots treated with the ROS/inducer mixture were marketable, as compared to 96% of the carrots grown after treatment with Vapam™. The ROS/inducer mixture also resulted in a yield of marketable carrots, 29.1 tons/acre, almost a ton per acre higher than did the fields treated with Vapam™, which produced 28.2 ton/acre. Thus, the method of the invention resulted in slightly better quality, and an increased yield, compared to a widely-used, but highly toxic, conventional pesticide.

b. Field Trial B

This trial was intended to measure the yield of "cello packs" of carrots, 50-pound plastic bags of carrots with their tops removed. "Cello pack"carrots command one of the highest prices the farmer can receive for carrots; it is advantageous to have carrots with a good weight and diameter so that fewer carrots are needed to fill each 50-pound bag. The trial was set up and conducted as for Field Trial A, above, including the size of the fields, the dates of application, and the concentrations of the agents applied. Carrots intended for cello pack, however, remain in the ground for an additional 10 days to allow them to gain more thickness and weight; this was done for each group in this trial.

Results: Pythium damaged 12.7% of the crop in fields treated with Vapam™ compared to almost zero (0.1%) in fields treated with the ROS/inducer mixture. Nematodes damaged 11.9% of the crop in fields treated with Vapam™ compared to 2.9% in fields treated with the ROS/inducer mixture. Accordingly, in replicate plots, the ROS/inducer markedly reduced damage from Pythium and nematodes compared to this widely used, but highly toxic, conventional pesticide.

The size of the carrots also differed between the two treatment groups. Nine percent more of the carrots grown in the fields treated with the ROS/inducer mixture had a diameter in the desirable ½ to 1 inch range compared to the carrots treated with Vapam™ (81% to 74%), while the percentage with diameters smaller than ½ inch in the ROS/inducer treated group was 4% smaller than that of the Vapam™ treated crop (19% to 23%). The ROS/inducer treated crop did have a smaller percentage of carrots with diameters over 1 inch compared to the Vapam™ treated crop (0% to 3%).

More importantly, the yield differed between the two treatment groups. Fields treated with the ROS/inducer mixture yielded 29 tons/acre, compared to 22.7 tons/acre produced by fields treated with Vapam™, a difference of almost 29%. Even more importantly, this difference in yield per acre was reflected in an almost 48% difference in the number of cello packs of carrots packed per acre, with an average of 177 bags per acre for the fields treated with the ROS/inducer mixture, and an average of 120 bags per acre for the fields treated with Vapam™. Thus, the method of the invention resulted in a markedly increased production of high value crop, compared to a widely-used, but highly toxic, conventional pesticide.

Example 8

Field Trial of the Invention to Determine Ability to Reduce Viral Damage to Tomatoes This trial shows the effect on the method of the invention on reducing damage to tomatoes from viral infections.

The trial plot comprised 84,000 square feet divided into 24 side-by-side replicates of treated and nontreated plants. Seventeen thousand four hundred plants were involved in the trial. Viruses present in the field were identified as: cucumber mosaic, alfalfa mosaic, and curly top. In addition, plants showed three different sets of symptoms which appeared to be due to viruses, but which could not be attributed to a specific virus.

Results: Treated plants showed an average of a 60.4% reduction in the incidence of virus symptoms compared to non-treated replicates.

Example 9

Field Trial of the Invention To Determine Ability to Reduce Downy Mildew Damage to Lettuce This trial shows the effect on the method of the invention on reducing damage to lettuce from downy mildew. Downy mildew is a fungal infection which causes lettuce to rot after harvest and is the greatest single problem in agricultural production of lettuce. It requires frequent treatment to keep it under control.

Plants treated with the PAA/inducer mixture were given foliar applications by overhead sprayer each at a rate of 16 oz. in 50 gallons of water per acre, in five applications each of which was spaced ten days apart. Control plants were given a combination of two conventional fungicides, Alliette™ and mancozeb, currently in wide use for controlling downy mildew in lettuce. The fungicides were also applied every ten days, following label directions. The plants were then compared for the number of leaves infected with downy mildew.

The results for a total of six replicates showed that, for the fields treated with the PAA/inducer mixture, a total of 45 plants were infected with downy mildew, and 704 were not, for an average infection rate of 6.1%. For plants treated with the conventional fungicides, a total of 117 plants were found to be infected out of 842 examined, for an average rate of infection of 12.2%. Thus, in this trial, treatment with a PAA/inducer mixture resulted in halving the infection of the plants by downy mildew.

Example 10

Two Field Trials of the Invention to Determine its Ability to Reduce Red Scale on Citrus Fruits These trials show the effect on the method of the invention on reducing damage to oranges from the insect pest red scale. The presence of red scale on the fruit renders it unmarketable for sale as fresh fruit and requires that the crop be sold at lower prices for use in juice. The insects also cause significant damage to the trees themselves. Evaluation of the number of insects on the leaves is a measure to determine the level of infestation on the trees before the insects reach the fruit.

a. Field Trial A

An orange grove was divided into two groups of trees, one to be treated with PAA/inducer and one to receive only an equivalent application of plain water. Trees to be treated with the PAA/inducer mixture were given a foliar application by sprayer, at a concentration of 2500 ppm, in 200 gallons of water per acre, a few weeks before harvest; and samples were taken for evaluation two weeks later. Five acres were treated. Three replicates were taken for each group of trees. Each replicate was made up of 10 leaves sampled from 5 trees, for a total of 50 leaves. Leaves selected for the sample were pulled from both the inside and the outside of the canopy of the trees. Insects present in addition to red scale were aphytis, predator mite, and lacewing; the numbers below, however, represent the numbers of red scale only.

Results: Among treated trees, 1173 live red scale insects were counted and 4833 dead red scale insects were counted, for a 20% to 80% (or 1:4) ratio of live to dead insects. Mortality was especially high among the earliest stages of the insect's life cycle: for example, only 5% of the crawlers were alive. Among control trees, treated only with water, 1637 live red scale insects were counted and 275 dead red scale insects were counted, for an 86% to 14% ratio. Ninety-six percent of the crawlers were alive. Thus, the application of the PAA/inducer mixture reversed the percentage of live to dead insects compared to the controls. Table 2 shows the percentages of dead insects by life stage for treated trees compared to untreated trees.

TABLE 2

| Life Stage | PAA/SA Treated % Dead | Untreated % Dead |
| --- | --- | --- |
| Crawlers | 95% | 4% |
| White Cap | 88% | 11% |
| Nipple/2nd Molt | 77% | 11% |
| Female: | 64% | 6% |
| Male: | 82% | 39% | b. Field Trial B

A second trial was run with the same application dates, concentrations, controls and sampling and evaluation criteria as reported for Field Trial A, above.

Results: As shown in Table 3, a high percentage of the insects found on the treated plants were dead in every life stage, with higher mortality among the earlier life stages. The untreated trees had a lower percentage of dead insects (and, hence, a larger percentage of live insects) at every life stage, with, for example, less than one fourth the percentage of dead insects in the nipple/2nd molt stage compared to the treated trees.

TABLE 3

| Life Stage | PAA/SA Treated % Dead | Untreated % Dead |
| --- | --- | --- |
| Crawlers | 97% | 52% |
| White Cap | 95% | 35% |
| Nipple/2nd Molt | 85% | 13% |
| Female: | 71% | 15% |
| Male: | 86% | 47% |

Example 11

Two Field Trials of the Invention to Determine Ability to Reduce Phylloxera and Nematode Infestation of Wine Grapes These trials show the effect on the method of the invention on reducing damage to two different varieties of wine grapes from phylloxera and from nematodes. Phylloxera is a root louse that deposits eggs in the soil; when they hatch, the offspring parasitize the plants.

a. Field Trial A

This trial was a phylloxera trial on grapes of the varietal Chardonnay. A one hundred-acre vineyard of this grape variety was divided into 2 fifty-acre plots. One portion of the vineyard was then treated with the PAA/inducer mixture a total of four times, by soil applications spaced 28 days apart. Each application was at a rate of ½ gallon of mixture per acre, to provide a concentration of 1900 ppm for 30 minutes. The other portion of the vineyard was treated with Enzone™, a pesticide commonly used to treat pholloxera infestation, following label directions.

Results: The PAA/inducer treated acres produced an average of 5.4 tons of grapes per acre. The nematicide-treated acres produced an average of 4.2 tons per acre. Thus, the acres treated according to the invention yielded approximately 28.5% more grapes per acres (in weight) than did comparable acres treated with a conventional agent.

b. Field Trial B

This trial was a nematode control trial on grapes of the varietal Zinfandel. The plots were selected and divided as in Field Trial A, above. The plots treated with the PAA/inducer mixture received the same treatment (that is, the same quantities and concentration of mixture, on the same dates) as did the plots described in Field Trial A of this Example, above. The control plots were treated with a conventional nematicide, DiTera™.

Results: The PAA/inducer treated acres produced an average of 4.52 tons of grapes per acre. The nematicide-treated acres produced an average of 3.49 tons per acre. Thus, the acres treated according to the invention yielded approximately 29.5% more grapes per acres (in weight) than did comparable acres treated with a conventional nematicide All publications, patents, and patent applications cited in this specification are herein incorporated by reference as if each individual publication, patent, or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of increasing disease resistance in a plant by increasing transcription of a gene encoding a protein selected from the group consisting of: a pathogenesis-related protein, phenylalanine ammonia lyase, chalcone synthase, and a hydroxyproline-rich glycoprotein, said method comprising contacting the plant with a plant systemic inducer and a reactive oxygen species, wherein the increase in disease resistance is greater than that caused by either the plant systemic inducer or the reactive oxygen species in the absence of the other.

2. A method of claim 1 wherein the increase in disease resistance is additive compared to the increase in disease resistance caused by the plant systemic inducer in the absence of the reactive oxygen species or by the reactive oxygen species in the absence of the plant systemic inducer.

3. A method of increasing, in a plant, transcription of a gene encoding a protein selected from the group consisting of: a pathogenesis-related protein, phenylalanine ammonia lyase, chalcone synthase, and a hydroxyproline-rich glycoprotein, comprising the step of contacting foliage of the plant with a plant systemic inducer and a reactive oxygen species wherein the amount of reactive oxygen species is sufficient to increase the level of transcription of said pathogenesis-related protein, phenylalanine ammonia lyase, chalcone synthase, or said hydroxyproline-rich glycoprotein above the level induced by the plant systemic inducer in the absence of the reactive oxygen species.

4. A method of claim 3 wherein the protein is a pathogenesis-related protein.

5. A method of claim 4 wherein the pathogenesis-related protein is the product of a PR-1 gene.

6. A method of claim 3 wherein the protein is phenylalanine ammonia lyase.

7. A method of claim 3 wherein the protein is a hydroxyproline-rich glycoprotein.

8. A method of claim 3 wherein the protein is chalcone synthase.

9. A method of claim 3, further wherein the plant is contacted with humic acid.

10. A method of claim 3, wherein the systemic inducer is derived from a kelp or other seaweed.

11. A method of claim 3 wherein the increase in the transcription of the pathogenesis-related protein, phenylalanine ammonia lyase, chalcone synthase, or hydroxyproline-rich glycoprotein by contacting the plant with both a plant systemic inducer and a reactive oxygen species is additive compared to the level of the transcription of the pathogenesis-related protein, phenylalanine ammonia lyase, chalcone synthase, or hydroxyproline-rich glycoprotein induced by either the plant systemic inducer in the absence of the reactive oxygen species or by the reactive oxygen species in the absence of the plant systemic inducer.

12. A method of claim 3 wherein the reactive oxygen species is selected from the group consisting of: peracetic acid, hydrogen peroxide, a hydroperoxide, a peroxide, calcium peroxide, potassium percarbonate, sodium percarbonate, and urea peroxide.

13. A method of claim 1 wherein the plant systemic inducer is selected from the group consisting of: salicylic acid, jasmonic acid, isonicotinic acid, arachidonic acid, phosphorus acid, dichloroisonicotinic acid, and benzothiadiazole.

14. A method of claim 3 wherein the plant systemic inducer is a microbe nonpathogenic to the plant.

15. A method of claim 3 wherein the plant systemic inducer is a microbe selected from the group consisting of: Bacillus, Serratia, Pseudomonas, and Trichoderna.

16. A method of claim 3 wherein the plant systemic inducer is salicylic acid.

17. A method of claim 3 wherein the plant systemic inducer is humic acid.

18. A method of claim 3 wherein the reactive oxygen species is peracetic acid.

19. A method of claim 3 wherein the plant systemic inducer species and the reactive oxygen species are mixed together before they contact the plant.

20. A method of claim 3 wherein the plant is a dicotyledon.

21. A method of claim 3 wherein the plant is a species edible by humans.

22. A method of claim 21 wherein the plant is selected from the group consisting of: lettuce, tomato, potato, corn, grape, carrot, legume, bean, strawberry, asparagus, and citrus fruit.

23. A method of claim 3 wherein the plant is selected from the group consisting of: turf grasses, cotton, rose, tulip, carnation, peony, begonia, daylily, lily, dahlia, hibiscus, azalea, dogwood, rhododendron, and iris.

24. A method of increasing, in a plant, transcription of a protein selected from the group consisting of: a pathogenesis-related protein, phenylalanine ammonia lyase, and a hydroxyproline-rich glycoprotein, comprising the step of contacting foliage of the plant with a plant systemic inducer and a reactive oxygen species wherein the amount of systemic inducer is sufficient to increase the level of transcription of said pathogenesis-related protein, phenylalanine ammonia lyase, or said hydroxyproline-rich glycoprotein above the level induced by the reactive oxygen species in the absence of the plant systemic inducer.

25. A method of claim 24 wherein the protein is a pathogenesis-related protein.

26. A method of claim 24 wherein the pathogenesis-related protein is the product of a PR-1 gene.

27. A method of claim 24 wherein the protein is phenylalanine ammonia lyase.

28. A method of claim 24 wherein the protein is a hydroxyproline-rich glycoprotein.

29. A method of claim 24 wherein the plant is a species edible by humans.

30. A method of claim 24 wherein the plant is selected from the group consisting of: lettuce, tomato, grape, potato, corn, carrot, legume, bean, strawberry, asparagus, and citrus fruit.

31. A method of claim 24 wherein the reactive oxygen species is selected from the group consisting of: peracetic acid, hydrogen peroxide, a hydroperoxide, a peroxide, calcium peroxide, potassium percarbonate, sodium percarbonate, and urea peroxide.

32. A method of claim 24 wherein the plant systemic inducer is selected from the group consisting of: salicylic acid, jasmonic acid, isonicotinic acid, arachidonic acid, dichloroisonicotinic acid, and benzothiadiazole.

33. A method of claim 24 wherein the plant systemic inducer is derived from kelp or another seaweed.

34. A method of claim 24 wherein the plant is contacted with humic acid.

35. A method of claim 3, wherein said contacting of the plant with a plant systemic inducer and a reactive oxygen species occurs for more than six hours in a ninety six hour period.

36. A method of increasing, in a plant, transcription of a protein selected from the group consisting of: a pathogenesis-related protein, phenylalanine ammonia lyase, and a hydroxyproline-rich glycoprotein, comprising the step of contacting roots of the plant with a plant systemic inducer and a reactive oxygen species wherein the amount of systemic inducer is sufficient to increase the level of transcription of said pathogenesis-related protein, phenylalanine ammonia lyase, or said hydroxyproline-rich glycoprotein above the level induced by the reactive oxygen species in the absence of the plant systemic inducer, provided that the composition does not comprise an agent selected from the group comprising a cation redox reducing agent and a divalent cation having redox potential in amounts sufficient to reduce the levels of microorganisms in soil around the roots by 40% or more.

37. A method of claim 36 wherein the protein is a pathogenesis-related protein.

38. A method of claim 36 wherein the pathogenesis-related protein is the product of a PR-1 gene.

39. A method of claim 36 wherein the protein is phenylalanine ammonia lyase.

40. A method of claim 36 wherein the protein is a hydroxyproline-rich glycoprotein.

41. A method of claim 36 wherein the plant is a species edible by humans.

42. A method of claim 36 wherein the plant is selected from the group consisting of: lettuce, tomato, grape, potato, corn, carrot, legume, bean, strawberry, asparagus, and citrus fruit.

43. A method of claim 36 wherein the reactive oxygen species is selected from the group consisting of: peracetic acid, hydrogen peroxide, a hydroperoxide, a peroxide, calcium peroxide, potassium percarbonate, sodium percarbonate, and urea peroxide.

44. A method of claim 36 wherein the plant systemic inducer is selected from the group consisting of: salicylic acid, jasmonic acid, isonicotinic acid, arachidonic acid, dichloroisonicotinic acid, and benzothiadiazole.

45. A method of claim 36 wherein the plant systemic inducer is derived from kelp or another seaweed.

46. A method of claim 36 wherein the plant is contacted with humic acid.

* * * * *